US005792210A

United States Patent [19]
Wamubu et al.

[11] Patent Number: 5,792,210
[45] Date of Patent: Aug. 11, 1998

[54] ELECTRICAL TONGUE STIMULATOR AND METHOD FOR ADDICTION TREATMENT

[75] Inventors: K'uu Lama Sa Wamubu, Milwaukee, Wis.; Kira Henschel, 4975 N. Woodruff Ave., Madison, Wis. 53217

[73] Assignees: Environmental Behavior Modification Inc., Milwaukee; Kira Henschel, Madison, both of Wis.

[21] Appl. No.: 664,998

[22] Filed: Jun. 10, 1996

[51] Int. Cl.$^6$ ................................. A61N 1/38
[52] U.S. Cl. ........................... 607/58; 607/900
[58] Field of Search ................. 607/40, 45, 58, 607/75, 76, 134, 900; 128/848

[56] References Cited

U.S. PATENT DOCUMENTS

| | | | |
|---|---|---|---|
| 3,277,892 | 10/1966 | Tepper | 607/58 |
| 3,889,163 | 6/1975 | Symmes | 607/58 |
| 4,841,973 | 6/1989 | Stecker | 607/900 |
| 5,190,053 | 3/1993 | Meer | 607/134 |
| 5,332,401 | 7/1994 | Davey et al. | 607/116 |
| 5,413,590 | 5/1995 | Williamson | 607/75 |
| 5,578,066 | 11/1996 | Gober | 607/58 |
| 5,607,461 | 3/1997 | Lathrop | 607/75 |

OTHER PUBLICATIONS

Abstract for "Inhibition of Gastric Acid Secretion in Man By the Transcranial Application of Two Intensity Pulsed Current"; Kotter et al., *Gastroenterology* 1975, Aug., pp. 359–363.

"Electrotherapeutic Sleep and Electroanesthesia," vol. V; Wageneder et al., *Fifth International Symposium in Graz*, pp. 285–287, 290–91.

Inhibition Of Gastric Acid Secretion In Man by The Transcranial Application Of Low Intensity Pulsed Current, Kotter et al., vol. 69, No. 2, Gastroenterology 69:359–363, 1975.

Respiratory Patterns During Application Of Transcranial Currents, Hamlton et al., source and date unknown.

*Primary Examiner*—William E. Kamm
*Assistant Examiner*—Carl H. Layno
*Attorney, Agent, or Firm*—Nilles & Nilles, S.C.

[57] ABSTRACT

A method and therapeutic apparatus for treating addictions and maladies, such as cocaine addiction and the like. In a preferred embodiment, the apparatus has a housing with a pair of exposed electrodes in communication with a current source that preferably is a battery. To provide suggestive reinforcement, the apparatus can have an indicia representative of the type of addiction or malady being treated. To further provide suggestive reinforcement, the housing of the apparatus can be constructed to visually appear suggestive of the addictive substance. During use, the apparatus is grasped by a user and brought toward the mouth until the electrodes engage a portion of the mouth that preferably is the tip of the tongue. In operation, electrical current flows through the tongue between electrodes and stimulates a nerve, that preferably is a hypoglossal nerve, in communication with the brain. As a result, cravings associated with an addiction or symptoms of a malady are curbed or disrupted thereby providing relief. Preferably, the cravings or symptoms diminish with repeated use of the apparatus. For an addiction, such as cocaine addiction, the treatment is administered using the apparatus every time a craving for the substance arises.

45 Claims, 4 Drawing Sheets

ELECTRICAL TONGUE STIMULATOR AND METHOD FOR ADDICTION TREATMENT

FIELD OF THE INVENTION

This invention relates generally to a method and therapeutic apparatus and more particularly to a method and apparatus for treating disorders, such as addictions, maladies and the like, by applying an electrical impulse to the mouth to stimulate nerves in the mouth.

BACKGROUND OF THE INVENTION

In the therapeutic treatment of maladies and disorders, drugs, surgery, counselling, as well as other techniques, are commonly used in an attempt to bring relief to the afflicted. For instance, pharmacological therapeutic treatments have been developed to treat neurological disorders, the central nervous system, renal disorders, gastrointestinal disorders, cancer, inflammation, microbial diseases, dermatological disorders, parasites, cardiovascular disorders, and other types of afflictions and disorders. Additionally, pharmacological therapeutic treatments have been developed to treat drug addiction and drug abuse. For example, some common types of drug addiction and drug abuse include: addiction to psychostimulants such as cocaine and amphetamines, opiate addiction, alcohol addiction, addiction to hypnotic drugs such as ethanol and barbiturates, morphine addiction, marijuana addiction, addiction to psychedelic drugs, and, of course, nicotine and tobacco addiction.

In addition to pharmacological treatment, counselling, psychological assistance, and psychiatric treatment are often used to treat these types of addictions. Unfortunately, the rate of successful treatment is relatively low for any heretofore known method or type of treatment for permanently breaking such addictions. It is known that many addicts relapse after long and expensive periods of anti-addiction treatment and therapy.

For example, cocaine addiction is but one type of addiction that is known to be difficult to successfully treat. During cocaine use, an afflicted person, known as a user or an addict, typically experiences a pleasurable feeling of an elevated mood, increased energy and alertness, and decreased appetite. It is believed that these pleasurable feelings are the result of cocaine's capacity to increase synaptic concentrations of dopamine by inhibiting dopamine uptake into neurons, particularly those neurons originating in the ventral segmental area of the brain projecting to such structures of the brain such as the nucleus accumbens, ventral palladium, and frontal cortex.

Typically, experienced cocaine users will taste cocaine to test its quality. Often, users report that the cocaine not only "tastes good", but also the act of tasting elicits a pleasurable feeling in the abdomen. This connection seems to indicate a link between the nerves transmitting the cocaine taste information to the brain and other nerves that are in communication with the brain and the gastrointestinal system.

After the effects of cocaine have worn off, a user often craves more cocaine. These cravings usually are intense urges that the user experiences, with the satisfaction of a craving, of course, being the acquisition and use of more cocaine. Many times these cravings for cocaine are so severe that they cause gastrointestinal rumblings, spasming, and hunger-like feelings in an addict.

In fact, the cravings in some cocaine addicts are so severe that they experience a strong seizure-like convulsion in the abdomen and empty their bowels simply in the eager anticipation of receiving cocaine. This intense reaction can occur simply by seeing, touching, smelling or tasting cocaine.

All of these types of cravings are believed to be generated by the brain of the addict in response to a desire for more cocaine. It is also believed that the nerves between the brain and stomach produce the aforementioned associated gastrointestinal phenomena when these types of cravings for cocaine arise. Therefore, although believed to be heretofore unknown, it is believed that there is a clear link between cravings for cocaine and the sensation of hunger in the abdomen, both of which originate in the brain.

Although believed to be heretofore unknown, it is postulated that at least some of the cravings arise in a portion of the brain, called the medulla oblongata, which is also responsible for sustenance of primitive or instinctive body functions, including those governing the desire to eat, to have sex, and other primitive or instinctive functions. It is further postulated that, at least in part, cravings for drugs such as cocaine originate, or are further developed, in the medulla oblongata and/or hypothalamus and are connected by these, or one or more, parts of the brain by nerves to the gastrointestinal system.

Unfortunately, as previously discussed herein, the treatment of people addicted to cocaine and other drugs has met with only limited success. Forms of treatment include: (1) drug therapy where other types of drugs are administered to break the addiction, (2) counselling, (3) psychiatric therapy, or (4) or combination of these regimens.

However, as is disclosed in a paper entitled *The Significance Of Current Frequency In Neuro-Electric Therapy (NET) For Drug And Alcohol Addictions*, which was authored by Margaret A. Patterson and published in 1978 in Volume V, *Electrotherapeutic Sleep and Electroanesthesia* (Fifth International Symposium In Graz), electrical current has been passed across the brain between the regions of the ears to treat heroin addiction. This method of delivering current across the brain by means of electrodes attached to the earlobes is referred to as transcranial electrotherapy (TCE or TCET). It is also disclosed in an article entitled *Inhibition of gastric acid secretion in man by the transcranial application of low intensity pulsed current*, published in the August 1975 issue of *Gastroenterology*, that TCE can be used to treat peptic ulcers.

Yet, it is not heretofore believed that any method or apparatus has been developed which uses the application of current applied orally to treat cocaine addiction. Moreover, it is also believed that no such method or apparatus has been developed which treats cocaine addiction by applying current to the mouth, and more specifically the tongue. Additionally, it is further believed that no method or apparatus for treating other forms of addictions, habits, and maladies, such as for example, drug addiction, sex addiction, food addiction, smoking, and chewing tobacco, has been developed which utilizes electrical current applied to the mouth, and more specifically the tongue.

SUMMARY OF THE INVENTION

A method and therapeutic apparatus for treating addictions, maladies, compulsions, and the like, with the apparatus having a pair of electrodes carried by a housing and in communication with an electric current source to provide an electric impulse to the electrodes during treatment. The electric impulse passes through soft tissues of the mouth, preferably the tongue, to stimulate nerves of the mouth in the treatment of the addiction or malady. Stimulation of oral nerves is communicated to the brain where addictive cravings or symptoms relating to maladies undergoing treatment are curbed and preferably eliminated.

Preferably, the apparatus can be used to treat addictions, such as addictions to drugs, alcohol, food and other behavior or substance addictions. Additionally, the apparatus is also well suited for treating gastrointestinal and eating disorders.

In one preferred embodiment of a therapeutic apparatus for treating cocaine addiction, the apparatus has a pair of spaced apart electrodes carried by a housing of a resilient and electrically insulating material. Each electrode is in communication with an electric current source that preferably is a direct current battery, such as a conventional nine volt battery that can be purchased in a department store. To make the apparatus transportable and easy to use, the housing has a hollow battery compartment for receiving the battery therein. To retain the battery in its compartment, the housing preferably also has a cover that can be easily removed to change the battery.

Adjacent the electrodes on the apparatus housing can be an indicia that preferably is the word "cocaine", or a cocaine related slang term, for providing suggestive reinforcement before and/or during treatment for directly associating the electrical impulse of treatment with curbing and preferably preventing cravings for cocaine. In a preferred circuit construction, the output terminals of the battery are directly connected to the electrodes by wires. If desired, the housing of the apparatus can be made to appear like a rock of cocaine, for example, to further reinforce treatment.

To secure the indicia to the housing the indicia can be imprinted on a label that is secured to the housing by a hook and loop fastener, another fastener, an adhesive, a wrapping that is heat shrunk tightly around the housing, or another method of securing the label to the housing. If used to treat another addiction or malady, the label can be removed and replaced with a different label having the desired indicia. If the apparatus is used to treat another person afflicted with a disorder or malady, the apparatus preferably can be easily cleaned and disinfected.

Preferably, the shape or appearance of the apparatus housing can be made to look like the addictive substance that is being treated. For example, the housing can be constructed and arranged to mimic a tin of chew or a package of cigarettes, if an addiction to tobacco is being treated. Of course, in the treatment of other addictions and maladies, other indicia and housing shapes can be used.

In a preferred circuit embodiment of the therapeutic apparatus, the electrodes are directly wired to the electric current source by wires. In a second preferred embodiment, an on-off switch is wired in series between the electrical current source and an electrode.

In a third circuit embodiment, a sub-circuit is electrically connected to the electric current source. Preferably, the sub-circuit can be constructed of a combination of conventional electric components for: (a) pulsing electrical current supplied to the electrodes, (b) oscillating electrical current supplied to the electrodes, (c) both pulsing and oscillating current supplied to the electrodes, (d) functioning as a power supply, (e) otherwise conditioning current supplied to the electrodes, (f) providing a reminder to use the apparatus such as by timer circuitry, or (g) performing another type of function.

In use and upon experiencing a craving or urge, the afflicted person grasps the housing of the therapeutic apparatus and brings it toward their mouth. Thereafter, the apparatus is positioned and oriented such that the electrodes of the apparatus are touched to the tip of the tongue of the afflicted or addicted person. As current flows through the tip of the tongue, nerves of the tongue in communication with the brain of the afflicted person are stimulated. Preferably, as current flows through the tip of the tongue and between electrodes, a hypoglossal nerve of the afflicted person is stimulated.

Preferably, stimulation of the hypoglossal nerve impacts the medulla oblongata of the afflicted person which in turn affects gastrointestinal nerves, at least one of which preferably is a vagus nerve. Preferably, the vagus nerve is ultimately affected by electrical stimulus from the therapeutic apparatus for helping to disrupt, curb or eliminate entirely any craving that an afflicted person possesses. Preferably, stimulus of the medulla oblongata and/or vagus nerve curbs any hunger related component of the craving that the afflicted person might possess.

Objects, features and advantages of this invention are to provide: a method and therapeutic apparatus for treating addictions, compulsions, bad habits, maladies, other disorders, and the like; a method which is simple and easy to administer; a method which is particularly well suited for treating cocaine addiction; a method that is versatile in that it can be used to treat other forms of drug addiction, gastrointestinal maladies, and eating disorders; an apparatus that is portable, transportable, light weight, easy to carry, and simple to use; an apparatus that is versatile in that it can be used to treat many addictions, maladies, and the like; an apparatus that can be easily cleaned and disinfected for repeated reuse; an apparatus that can be quickly, easily, and inexpensively tailored to treat a specific addiction or malady; and a therapeutic apparatus that is rugged, simple, flexible, reliable, and durable, and which is of economical manufacture and is easy to assemble and use.

BRIEF DESCRIPTION OF THE DRAWINGS

These and other objects, features, and advantages of this invention will become apparent from the following detailed description of the best mode, appended claims, and accompanying drawings in which:

DETAILED DESCRIPTION OF THE INVENTION

Figure 1:
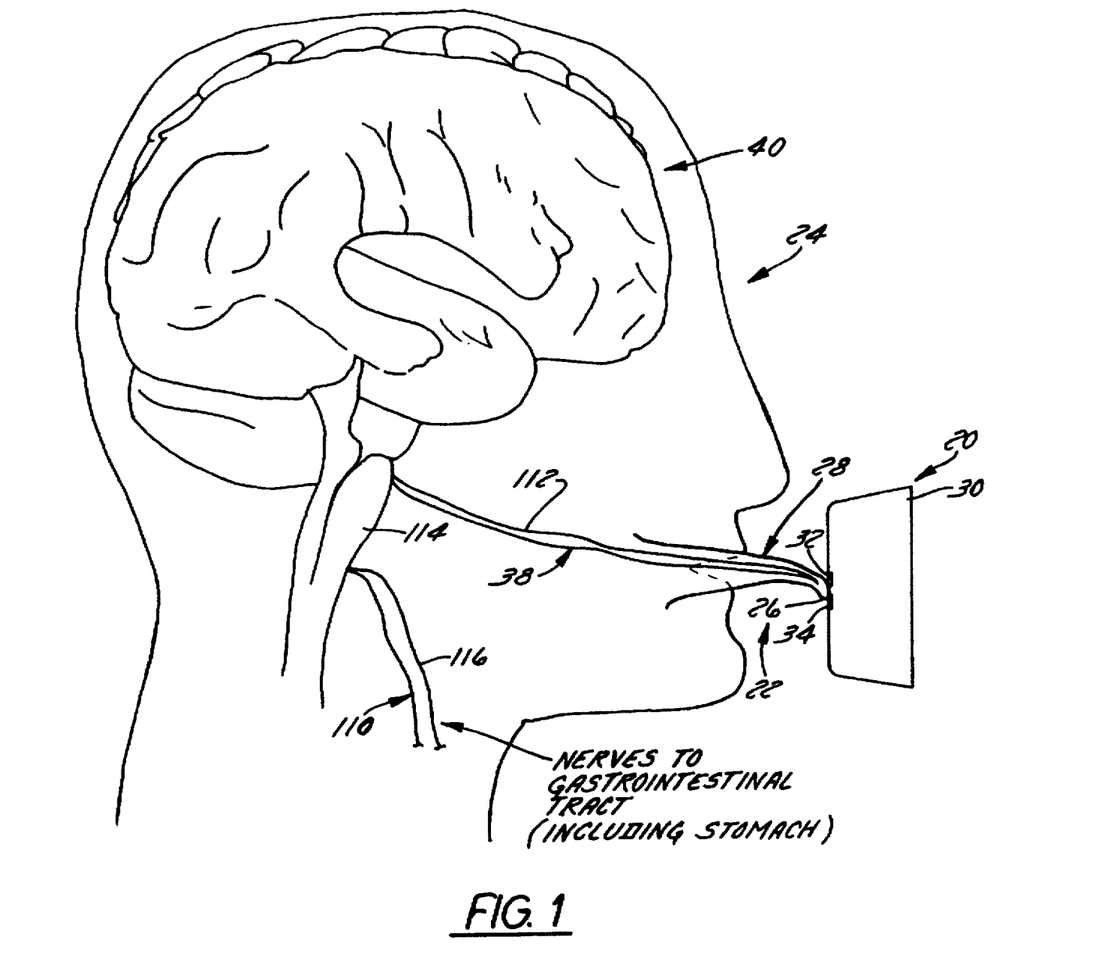
FIG. 1 is a side view of a therapeutic apparatus of this invention applying an electric impulse to the tip of the tongue of a person being treated by the apparatus.

FIG. 1 illustrates a therapeutic apparatus 20 of this invention for treating maladies related to eating and the gastrointestinal tract, addictions, as well as bad habits and other compulsions, by introducing an electrical impulse to a portion of the mouth 22 of an afflicted person 24 to be treated that preferably is the tip 26 of the tongue 28. The apparatus 20 has a housing 30 which carries a pair of spaced apart and exposed electrodes 32 & 34 which are in electrical communication with a source of electrical current 36 (FIGS. 3 & 4).

In use, the afflicted person 24 seeking treatment administers an electrical impulse by placing both electrodes 32 & 34 of the apparatus 20 in contact with the tongue 28 for administering a dose of electrical current to the tongue 28. Preferably, the electrical current stimulates at least one nerve 38 in communication with the brain 40 of the person 24 for treating their malady or addiction.

Figure 2:
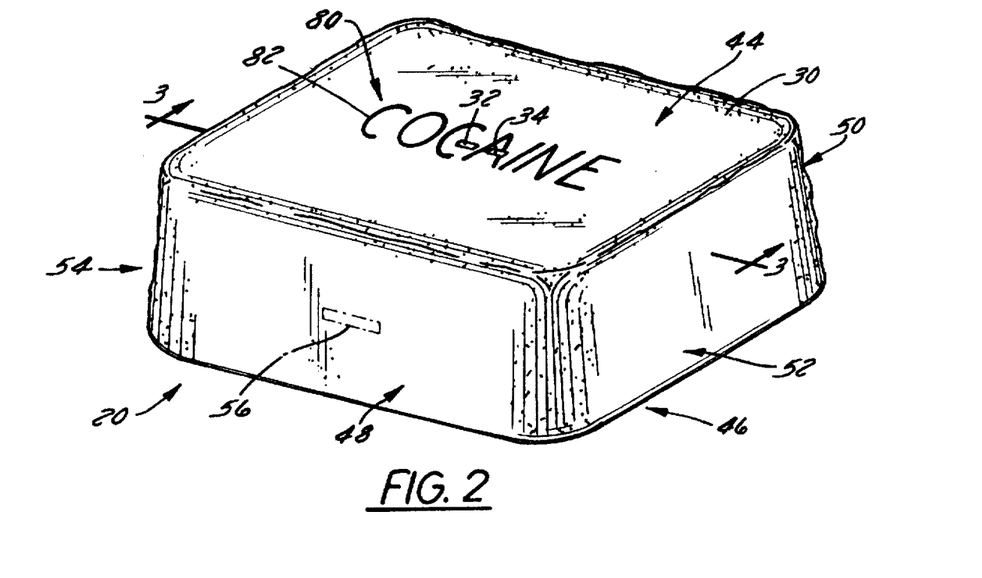
FIG. 2 is a top perspective view of a preferred embodiment of the therapeutic apparatus of this invention.
Figure 3:
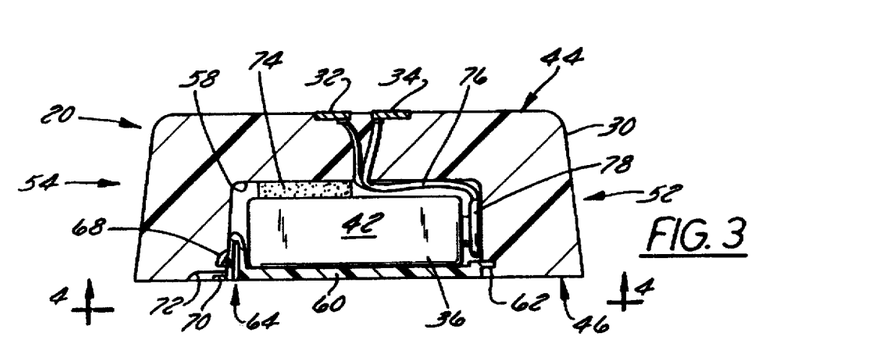
FIG. 3 is a cross sectional view of the apparatus taken along line 3—3 of FIG. 2.
Figure 4:
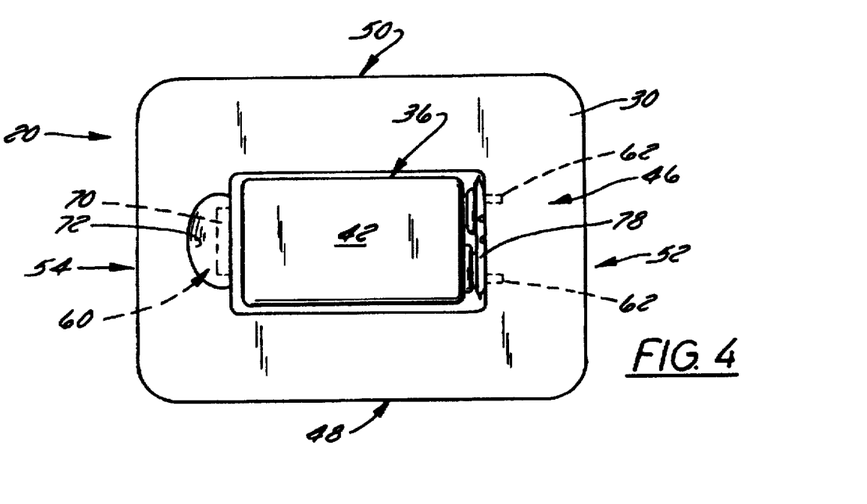
FIG. 4 is a bottom plan view of the apparatus in the direction of line 4—4 of FIG. 3 with a cover of the apparatus shown in phantom for showing a battery that is a source of current for the apparatus.
Figure 5:
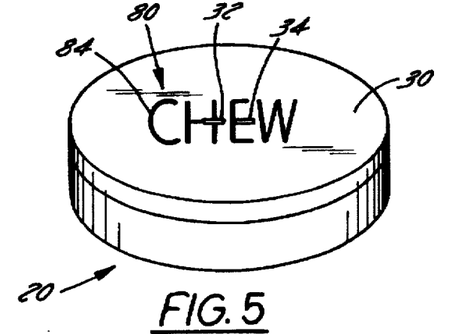
FIG. 5 is a top perspective view of one preferred embodiment of a housing of the apparatus with the housing shaped to mimic a tin of chewing tobacco.
Figure 6:
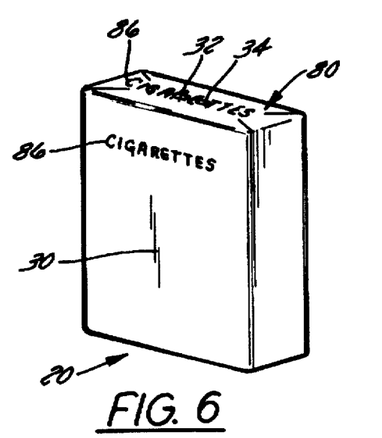
FIG. 6 is a perspective view of another preferred embodiment of a housing of the apparatus with the housing shaped to appear like a package of cigarettes.

Referring to FIGS. 2–4, an embodiment of the apparatus 20 for treating an addiction to cocaine is illustrated. The apparatus 20 has a housing 30 with a pair of spaced apart electrodes 32 & 34 exposed exteriorly of the housing 30 for contact with a part or portion of the mouth 22 of a person 24 being treated for cocaine addiction. The electrodes 32 & 34 are electrically connected to the electrical power or current source 36. As is depicted in FIGS. 3 & 4, the electrical current source 36 preferably is a battery 42.

As is shown in FIGS. 2 & 4, the housing 30 has a top surface 44, a bottom surface 46, a front surface 48, a rear surface 50, a right side surface 52 and a left side surface 54. Although the electrodes 32 & 34 are shown on the top surface 44, the electrodes 32 & 34 can be located in another position, such as is shown in FIG. 2 by the rectangle 56 in phantom on the front surface 48 or in FIG. 7. Alternatively, the rectangle 56 shown in phantom in FIG. 2 could also be the location for an on-off switch (not shown) of the apparatus 20, should such a switch be desired.

Preferably, as is depicted in FIG. 3, the housing 30 has a hollow compartment 58 for receiving the battery 42 therein. To retain the battery 42 in the compartment 58, the housing 30 has a cover 60 (shown in phantom in FIG. 4) which is removably secured to the housing 30 and overlies the compartment 58. When assembled, the housing 30, battery 42, electrodes 32 & 34, and cover 60 form a unitary assembly of one-piece construction that is of relatively compact and lightweight construction for hand-held use. Preferably, the entire therapeutic apparatus assembly can be constructed so it weighs less than about one pound so that it can be easily carried by the afflicted person 24 and can be easily held and manipulated by the afflicted person 24 to self-administer treatment using the apparatus 20.

For long lasting and reliable operation, the housing 30 is constructed of a durable and resilient material. One such preferred material is a plastic, such as a nylon, a thermoplastic, a thermoset, a recycled plastic, or another type of plastic. In any event, the housing 30 is preferably constructed of a material which facilitates easy and sanitary cleaning of the entire apparatus 20 for enabling an apparatus 20 it to be reused to treat another patient after an afflicted patient 24 has been cured. Preferably, the apparatus 20 can be cleaned, disinfected, and reused many times before requiring disposal.

If made of plastic, the housing 30 is preferably molded, such as by an injection molding process, a vacuum molding process, or another type of molding or forming process. Alternatively, the housing 30 can be constructed of wood, a ceramic, a composite, or another suitably durable and resilient material. If constructed of a metal, there preferably is electrical insulation between the housing 30 and each electrode 32 & 34.

Preferably, the cover 60 can be of snap-fit construction for being positively, securely, and releasably secured to the housing 30 so that the battery 42 can be securely retained in its compartment 58 while enabling the cover 60 to be easily removed to change the battery 42 should a new battery be needed. Alternatively, the cover 60 can be constructed with a locking device or a seal to prevent easy removal of the cover 60, such as for making the therapeutic apparatus 20 tamper-proof.

In one preferred cover embodiment 60 shown in FIG. 3, at one end, the cover 60 has outwardly projecting fingers 62 that are received in a complementary pockets in the housing 30. To releasably secure the cover 60 to the housing 30, the other end of the cover has a latch 64. The latch 64 preferably is comprised of a generally U-shaped and resiliently outwardly biased catch 66 that has a pawl 68 received in a complementary detent in the housing 30 when the cover 60 is completely closed. To release the cover 60 so it can be removed, adjacent the pawl 68 there is an outwardly extending release flange 70 that can be engaged by a finger or fingernail to urge the catch 66 away from the housing 30 to disengage the pawl 68 from the detent. So that a finger or fingernail can easily engage the release flange 70, the housing 30 has a relief depression 72 in its bottom surface 46.

To prevent the battery 42 from freely moving about within the compartment 58, there preferably is a flexible and resilient pad 74 between an interior wall of the compartment 58 and the exterior of the battery 42. The pad 74 is of a sufficient thickness such that it urges the battery 42 against the cover 60 when the cover 60 is closed. If desired, the pad 74 can be constructed of an open or closed cell foam for helping to prevent movement of the battery 42 within the battery compartment 58.

In the preferred embodiment of an electrical current source 36 depicted in FIGS. 2–4, the electrical current source 36 is a battery 42 that preferably is a nine-volt direct current battery. Alternatively, the battery 42 can be another type of direct current battery, such as a 1.5 volt battery of size A, AA, C or D, for example. If desired, one or more batteries can be combined in series or parallel, depending upon the desired voltage or current required to be supplied to the electrodes 32 & 34. Additionally, the battery 42 can be of conventional construction or the battery 42 can be a nickel-cadmium battery, a nickel-hydride battery, a lead-acid battery, or another type of battery.

If desired, electric current power source 36 can be another source such as an alternating current source. For example, an alternating current source can be rectified to produce direct current, if it is necessary or desirable. If not, alternating current (A.C.) can be directly supplied to the electrodes 32 & 34, if desired. To promote environmental responsibility, the housing preferably can also be constructed with a built-in battery recharging circuit and a cord for plugging the recharging circuit into a 120 volt A.C. outlet (not shown). In this manner, a rechargeable battery can be used to supply current to the electrodes 32 & 34 and periodically be recharged by simply plugging the cord into an A.C. outlet. If a rechargeable battery and recharger are incorporated into the housing 30 of the apparatus 20, the battery 42 preferably can be permanently sealed within the housing 30.

In the preferred embodiment of the therapeutic apparatus shown in FIGS. 2–4, the current source 36 supplies to the electrodes 32 & 34 a current of no greater than about a few hundred milliamperes and no greater than about one ampere. Depending upon the application, more or less current may be required. If a nine-volt battery is used, current directly from the battery 42 can be delivered through the electrodes 32 & 34 to the afflicted person 24. However, a combination of one or more resistors, capacitors, diodes, and other electrical components can be used to control or vary the magnitude and intensity of the electrical impulse supplied to the electrodes 32 & 34.

In the embodiment of the therapeutic apparatus shown in FIGS. 3 & 4, the battery 42 is directly connected to the electrodes 32 & 34 by a wiring harness 76. Preferably, the wiring harness 76 can be simply comprised of a pair of wires. Preferably, the wiring harness 76 has a snap-on connector 78 at one end for direct connection to output terminals of the battery 42. At its other end, if directly connected to the battery output terminals, individual wires of the harness 76 can be directly connected to each electrode 32 & 34, such as by soldering.

As is shown more clearly in FIGS. 2 & 3, each electrode 32 & 34 is carried by the housing 30 with at least a portion of each electrode exposed exteriorly of the housing 30 so that a portion of the mouth and/or the tongue of an afflicted person 24 can make contact with each electrode 32 & 34 during treatment. Preferably, each electrode 32 & 34 is constructed of an electrically conductive material, such as a stainless steel, a steel, a copper, silver, gold, or another electrically conductive material that does not necessarily have to be a metal.

To ensure current flow through the mouth 22 or tongue 28, the electrodes 32 & 34 are spaced apart by at least about one millimeter and are preferably spaced apart by more than one millimeter. To prevent current from flowing directly between the electrodes 32 & 34 and not through any portion of the mouth 22 or tongue 28, there is an electrically insulating material between the electrodes 32 & 34. To prevent short circuiting between the electrodes 32 & 34, the housing 30 can be constructed of an electrically insulating material.

Preferably, the electrodes 32 & 34 are spaced apart no greater than about one and one-half inches so that both electrodes 32 & 34 can make contact with a portion of either the mouth 22 or tongue 28 of a person 24 undergoing treatment. For example, when administering therapeutic treatment by touching the electrodes 32 & 34 to the tip 26 of the tongue 28, the electrodes 32 & 34 can be spaced apart between about a millimeter up to about three centimeters.

For the housing 30 shown in FIGS. 2 & 3, each electrode 32 & 34 is generally flush with the exterior surface of the housing 30. If desired, the therapeutic apparatus 20 can be constructed with electrodes that extend outwardly from an exterior surface of the housing 30. If desired, the electrodes 32 & 34 preferably can be constructed and arranged such that they can be extended outwardly for use and thereafter be retracted into the housing 30.

To facilitate easy cleaning and to promote sanitary use, the electrodes 32 & 34 can be situated in a depression (not shown) in an exterior surface of the housing 30 and be covered with a sanitary medium such as a film having electrically conducting portions in communication with each electrode. To prevent short circuiting, however, there preferably is at least some electrically insulating material between the electrodes 32 & 34.

Referring to FIGS. 2 and 5–7, an indicia 80, in the form of a word, phrase, message, image, or symbol can be secured to, carried by, applied to, imprinted on, or molded into an exterior surface of the therapeutic apparatus housing 30. For example, as is shown in FIG. 2, the word "cocaine" 82 is molded into the top surface 44 of the housing 30. For the therapeutic apparatus 20 shown in FIG. 5, the word "chew" 84 can be silk-screened onto the top surface 44 of the housing 30. For the embodiments of the therapeutic apparatus 20 shown in FIGS. 7 & 8, the indicia 80 is placed on a label that is secured to the housing.

Preferably, the indicia 80 is in the form of a name that generally identifies or alludes to the addiction or malady being treated. For example, as is shown in FIG. 2, the indicia 80 is in the form of the word "cocaine" 82 to suggest to an afflicted person being treated for cocaine addiction that the apparatus 20 is suggestive of cocaine so that treatments using the apparatus 20 associate cocaine with an electrical current, impulse, or shock from the electrodes 32 & 34, when touched to the mouth or tongue. Similarly, the indicia 80 can be the word (1) "chew" 84, for a person attempting to break an addiction to chewing tobacco, (2) the word "cigarettes" 86, for someone attempting to quit smoking, (3) the word "candy" 88, for someone trying to curb or eliminate eating candy, or (4) yet another word representative or suggestive of another addiction that can be treated with the therapeutic apparatus 20 of this invention. Examples of other types of indicia 80 which can be used are: crack, crank, smack, dope, alcohol, vodka, brandy, whiskey, wine, beer, morphine, amphetamines, speed, methamphetamine, heroin, barbiturates, LSD, psychedelic drugs, sex, food, caffeine, nicotine, tobacco or another type of addiction. Additionally, slang names for any of these and other addictions are also types of indicia contemplated within the scope of the therapeutic apparatus 20 of this invention.

Figure 7:
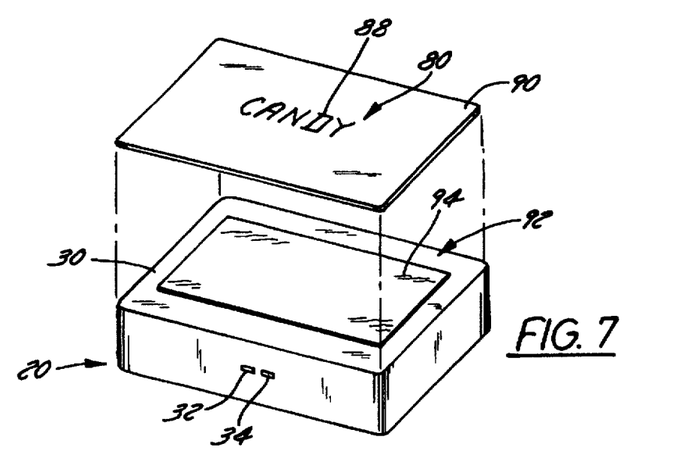
FIG. 7 is a top exploded perspective view of a preferred embodiment of the apparatus having a label with an indicia thereon secured to the housing of the apparatus by a fastener.
Figure 8:
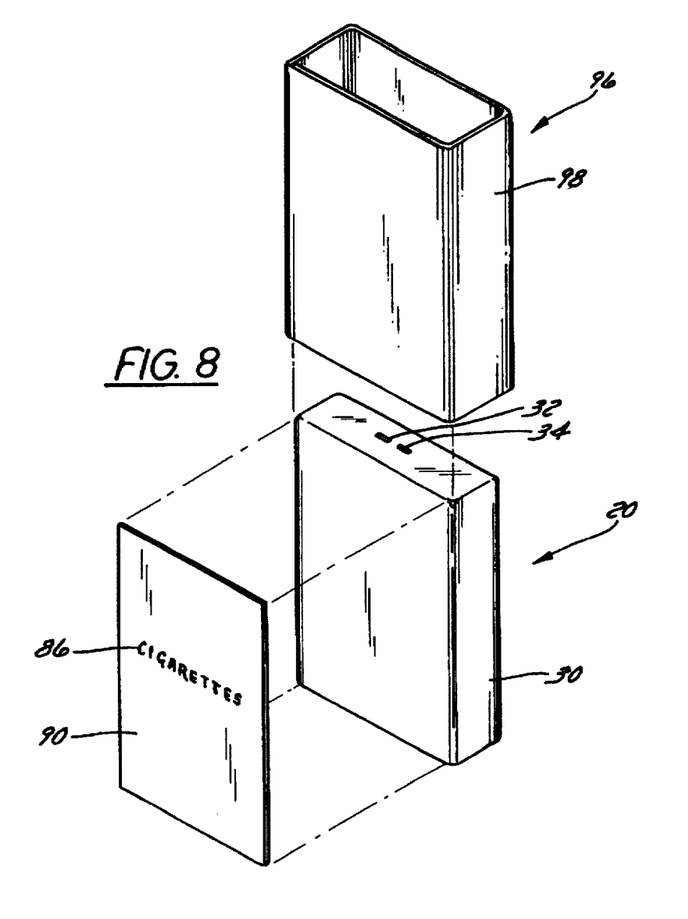
FIG. 8 is an exploded perspective view of a preferred embodiment of the apparatus having a label with an indicia thereon secured to the housing of the apparatus by a tube of clear wrap that is shrunk around the housing.

The therapeutic apparatus 20 can be constructed in the manner shown in FIGS. 7 & 8 having the indicia 80 is placed on a label 90 that is secured to the housing 30 of the apparatus 20. As is shown in FIG. 7, the indicia 80 is the word "candy" 88 which is printed on a label 90 that is secured to the housing 30 using a fastener 92 that preferably is a hook and loop type fastener 94, such as VELCRO. Advantageously, this enables the apparatus 20 to be used to treat different addictions and maladies simply by changing the label 90 and/or indicia 80. If desired, another fastener 92 can be used or, if permanency is desired, an adhesive could be used to apply the label 90 directly to the housing 30. If desired, the indicia 80 can be directly silk screened onto or printed on an exterior surface of the apparatus housing 30.

As is shown in FIG. 8, the indicia "cigarettes", applied on label 90, is secured to the housing 30 of the apparatus 20 by a tube 96 constructed of a clear material 98 that preferably is shrunk tightly around the label 90 and housing 30. Preferably, the material 98 is a clear heat shrinkable plastic that is placed over the housing 30 of the apparatus 20 to hold the label 90 in place against the housing 30. After treatment of an afflicted person 24 has been completed, the wrapping 96 can be removed and the procedure repeated if it is desired to place a another or different label 90 containing another indicia 80 on the apparatus housing 30 to treat another type of addiction or malady.

Figure 9:
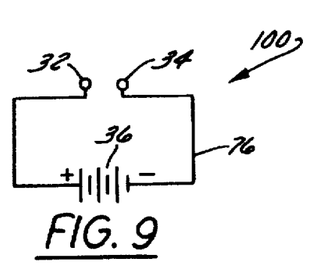
FIG. 9 is a schematic diagram depicting one preferred embodiment of a circuit for the apparatus.
Figure 10:
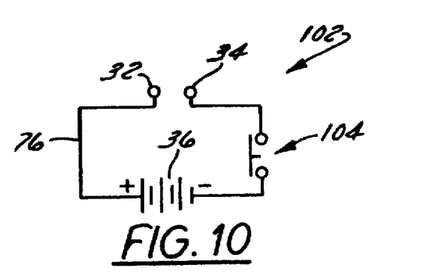
FIG. 10 is a second schematic diagram depicting another preferred circuit embodiment having a switch between the current source and an electrode for enabling selective operation of the apparatus.
Figure 11:
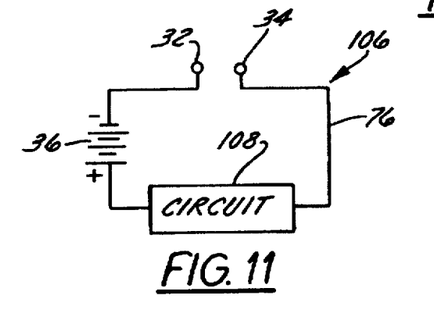
FIG. 11 is a third schematic diagram depicting a still further circuit embodiment having a sub-circuit in electrical communication with the current source.

FIGS. 9–11 illustrate preferred embodiments of circuitry for enabling operation of the apparatus 20. In a first preferred embodiment of a therapeutic apparatus circuit 100 depicted in FIG. 9, the circuit 100 consists of an electrical current source 36 that is connected by a pair of wires 76 to the electrodes 32 & 34. In a second preferred embodiment of a therapeutic apparatus circuit 102 depicted in FIG. 10, the circuit has a switch 104 between the current source 36 and an electrode.

In a third preferred embodiment of a therapeutic apparatus circuit 106 shown in FIG. 11, the circuit 106 has a sub-circuit 108 in electrical communication with the electrical power source 36. Although the sub-circuit 108 is depicted as being wired in series between the current source 36 and an electrode, the sub-circuit 108 can also be constructed and arranged so that it is wired in parallel, a combination thereof, or wired or connected in another manner. Preferably, the sub-circuit 108 can be a circuit for shaping, varying, regulating, or controlling the magnitude or duration of current applied to an afflicted person 24 during therapeutic treatment. Alternatively, the sub-circuit 108 can be a power supply for controllably supplying current at a desired voltage to the electrodes 32 & 34.

For example, the sub-circuit 108 can be a circuit that uses one or more of the following: resistors, diodes, capacitors, semiconductor switching devices, triacs, SCRs, transistors, integrated circuit chips, and other types of electrical components to control, shape, vary, or regulate the current flowing to one or both electrodes 32 & 34. Such a sub-circuit 108 can be constructed and arranged to pulse current applied to the electrodes 32 & 34 in a manner similar to that effected by a conventional pulsing electrical power supply. If pulsed current is produced by the sub-circuit 108, its duration, magnitude and frequency preferably can be controlled. Preferably, the desired pulse duration, magnitude and frequency can be determined for a particular addiction or malady to be treated by routine testing and experimentation.

Additionally, such a sub-circuit 108 preferably can be constructed and arranged to oscillate electric current applied to the electrodes 32 & 34. If current is oscillated, its frequency of oscillation preferably can be at least about one hertz or greater. For example, the sub-circuit 108 can be constructed and arranged to provide current to the electrodes 32 & 34 at a frequency of several kilohertz, if desired. Preferably, the desired frequency can be determined by routine testing and experimentation. If desired, the sub-circuit 108 can be a circuit that both pulses and oscillates current delivered to one or both electrodes.

In a still further sub-circuit construction, the sub-circuit 108 can be constructed and arranged to be in electrical communication with the electric current source 36 to provide means for stimulating a person 24 carrying the therapeutic apparatus 20 to remind them to use it at certain predetermined time periods during the hour, day, week, month or year. Such a sub-circuit 108 can comprise an alarm powered by the electrical current source 36 or an independent electrical current source (not shown) for reminding the person 24 carrying the apparatus 20 it is time to use the apparatus 20 as part of the treatment regimen.

Such a reminder sub-circuit can be comprised of a timer circuit in electrical communication with a buzzer or vibrator for generating a reminder to use the apparatus. For example, an I-555 timer can be coupled to an electromechanical device for causing the therapeutic apparatus 20 to shake or buzz while in the pocket of a person 24 carrying the apparatus 20 to discreetly and unobtrusively remind the person 24 it is time to use the apparatus 20. Additionally, other sub-circuit constructions and arrangements are possible.

Use and Operation

In use, a therapeutic apparatus 20 of this invention is preferably used to treat cocaine addiction. Additionally, a therapeutic apparatus 20 of this invention is also well suited for treating other types of addictions, including: amphetamine addiction, alcoholism, morphine addiction, addiction to pain killers, heroin addiction, food addiction, caffeine addiction, barbiturate addiction, marijuana addiction, and addiction to prescription drugs, addiction to nicotine, addiction to over-the-counter drugs and chewing tobacco addiction. Preferably, the therapeutic apparatus 20 of this invention also can be used for treating other types of addictions or compulsions not involving substances, such as for example, sex addiction.

Preferably, a therapeutic apparatus 20 of this invention can also be used for treating other disorders or maladies related to the gastrointestinal tract, such as: an ulcer, a peptic ulcer, gastritis, stomach pain, chronic stomach pain, heartburn, hiatal hernias, excess stomach acid production, or another stomach, gastric or gastrointestinal related disorder. Preferably, gastrointestinal is intended to include the small intestine, large intestine and colon. Additionally, a therapeutic apparatus 20 of this invention is also well suited for treating eating disorders such as anorexia or bulimia.

In operation, a user of the therapeutic apparatus 20, preferably a person 24 afflicted with an aforementioned addiction or malady, grasps the housing 30 of the apparatus 20 and brings it near their mouth 22. To administer therapeutic treatment, the electrodes 32 & 34 of the apparatus 20 are brought into contact with a portion of the mouth 22 whereby electrical current is passed from one electrode, through the mouth, and to the other electrode.

As current passes through the mouth, the current stimulates nerves, such as nerve 38 shown in FIG. 1, which communicate with the brain 40. As a result of directly stimulating the brain 40, therapeutic treatment is administered.

In the case of an addiction, the stimulation of nerves of the mouth reduces and preferably prevents cravings for the substance desired by the afflicted person 24. Therefore, the therapeutic apparatus 20 is intended to be used when an afflicted person 24 is experiencing cravings for a particular substance. Additionally, the apparatus 20 can be used at other times, such as for preventing the onset of a craving.

Preferably, the apparatus 20 can be shaped to provide to the afflicted person 24 a suggestion representative of the affliction to be treated for providing a powerful psychological reinforcing message before, during and/or in conjunction with treatment. For example, the housing 30 of the apparatus 20 can be shaped or made to appear like a package of cigarettes (FIGS. 6 & 8) to provide visual reinforcement for an afflicted person 24 to assist them in breaking an addiction to cigarettes. Preferably, the indicia "cigarettes" also aids in psychologically reinforcing the therapeutic treatment of the apparatus 20. By seeing the shape of the housing 30 and/or indicia of the therapeutic apparatus before administering an electrical impulse, the application of an electrical impulse by the electrodes 32 & 34 carries great effect in reducing and preventing cravings, the goal of which is to ultimately end the addiction.

By administering an electrical impulse, preferably in the form of electrical current flow, every time a craving occurs, the apparatus 20 repeatedly disrupts the craving by stimulating nerves 38 in communication with the brain 40. By providing a housing 30 suggestive of the addiction being treated, the application of electrical current is preferably thereby also associated by the afflicted person 24 with the addiction being treated. Alone, the application of current is effective. In combination with imagery-based suggestion, the application of current is preferably even more effective.

In the case of a gastrointestinal disorder, stimulation of nerves of the mouth is preferably self-administered by an afflicted person 24 whenever the need arises. For example, to prevent heartburn, an afflicted person 24 preferably self-administers therapeutic treatment using the apparatus 20 when the person 24 feels the onset of certain symptoms which typically lead to heartburn. For other types of gastrointestinal disorders, an afflicted person 24 preferably self-administers treatment at the onset of certain symptoms that are predictive of the gastrointestinal disorder being treated.

For an eating disorder, such as anexoria or bulimia, treatment is preferably administered whenever the afflicted person begins experiencing the thoughts which are directly causal of the eating disorder. In this manner, the undesirable thought processes are at least briefly disrupted upon the application of the therapeutic electrical impulse to the mouth.

Preferably, during use of the therapeutic apparatus 20, both electrodes 32 & 34 are brought in contact with the tongue 28 to cause electrical current to flow through the tongue 28 between the electrodes 32 & 34. Preferably, the electrodes 32 & 34 are both brought into contact with the tip 26 of the tongue 28 for stimulating nerves in the tip 26 of the tongue 28.

As is shown more clearly in FIG. 1, as an afflicted person 24 touches the electrodes 32 & 34 to the tip 26 of the tongue area 28, an electrical current flows through the tip 26 of the tongue 28 thereby stimulating at least one nerve 38 that is in communication with the brain 40 of the afflicted person 24. Although, the afflicted person 24 preferably extends their tongue 28 outwardly from their mouth 22 to make contact with the electrodes 32 & 34, the therapeutic apparatus 20 preferably also can be constructed and arranged so that it contacts the tongue 28 while the tongue 28 is inside the mouth 22 of the afflicted person 24.

This stimulating electrical impulse preferably briefly disrupts the thought process of the afflicted person 24 so that they no longer strongly feel the craving or symptom that they previously were experiencing. For some types of addictions and maladies, stimulation of tongue nerves 38 preferably stimulates the brain 40, which in turn communicates with at least one gastrointestinal nerve 110 to provide relief and further treatment.

Cocaine Addiction

For the treatment of cocaine addiction, an embodiment of the therapeutic apparatus 20 of this invention constructed in the manner shown in FIGS. 2–4 is used. Preferably, the apparatus housing 30 carries the word "cocaine" adjacent the electrodes 32 & 34 to provide powerful suggestive reinforcement before treatment is administered by a person 24 afflicted with an addiction to cocaine. As an electrical current source 36, a conventional nine volt battery is used. Preferably, each terminal of the battery 42 is directly wired to an electrode.

During use, referring additionally to FIG. 1, the afflicted cocaine addict 24 carries the therapeutic apparatus 20 inside a pocket of a garment being worn by the addict 24. Whenever the addict 24 experiences an urge or craving for cocaine, the addict 24 reaches into their pocket, pulls the apparatus 20 out of the pocket and glances at the apparatus 20 before bringing it toward their mouth 22. By seeing the word "cocaine", the administration of treatment by the apparatus 20 is immediately and powerfully linked to the addiction, thereby providing suggestive reinforcement immediately before use of the therapeutic apparatus 20.

To administer treatment, both electrodes 32 & 34 of the apparatus 20 are brought to bear preferably against the tip 26 of the tongue 28 of the cocaine addict 24. When both electrodes 32 & 34 are in contact with the tongue 28, electrical current flows through the tip 26 of the tongue 28 between the electrodes 32 & 34. Preferably, the apparatus 20 is held against the tongue 28 for a sufficient duration of time to cause the urge or craving for cocaine to diminish. Preferably, the electrodes 32 & 34 are held in electrically conductive contact with the tongue 28 for at least an instant, that can be as long as one second or more.

As electrical current passes through the tongue 28, it stimulates nerves 38 which are in communication with the brain 40. One such nerve that the electrical impulse from the therapeutic apparatus stimulates is a nerve known as the hypoglossal or "12th" nerve 112. Since the hypoglossal nerve 112 is tied to the medulla oblongata 114 portion of the brain 40, the electrical impulse preferably also causes stimulation the vagus nerve 116 which extends to the gastrointestinal tract to help treat the apparent hunger for cocaine some addicts experience in their abdomen. With consistent and repeated use of the therapeutic apparatus 20, cravings for cocaine will preferably become less frequent and less powerful until the once afflicted person 24 is no longer addicted.

It is also to be understood that, although the foregoing description and drawings describe and illustrate in detail one or more embodiments of the present invention, to those skilled in the art to which the present invention relates, the present disclosure will suggest many modifications and constructions as well as widely differing embodiments and applications without thereby departing from the spirit and scope of the invention. The present invention, therefore, is intended to be limited only by the scope of the appended claims and the applicable prior art.

What is claimed is:

1. An apparatus for applying an electrical impulse to the mouth of a person having a tongue comprising:
   (a) a housing;
   (b) a source of electrical current;
   (c) a pair of spaced apart electrodes carried by said housing and which are electrically connected to said electrical source for delivering an electrical impulse to the mouth when both of said electrodes are in contact with the mouth;
   (e) wherein said housing and electrodes form an assembly of unitary construction that is grasped by hand during use; and
   (f) wherein said electrodes and housing are constructed and arranged to deliver said electrical impulse to the tongue of the person.

2. The apparatus of claim 1 wherein said housing has a hollow compartment for receiving said electrical current source and further comprising a cover for engaging said housing to retain said electrical current source within said compartment.

3. The apparatus of claim 2 wherein said electrical current source comprises a direct current battery.

4. The apparatus of claim 2 wherein said housing is comprised of an electrically insulating plastic.

5. The apparatus of claim 3 wherein said electrodes are spaced apart at least about one millimeter and no greater than about two centimeters for enabling said electrical impulse to be administered to the tip of the tongue of the person.

6. The apparatus of claim 5 further comprising a label secured to said housing by 1) a hook and loop fastener, or 2) a generally transparent sheet or tube of shrink wrapping.

7. The apparatus of claim 3 wherein said electrical current source comprises a nine volt battery.

8. The apparatus of claim 1 further comprising a circuit in electrical communication with said electrical current source and said electrodes.

9. The apparatus of claim 8 further comprising means for switching electric current flow to the electrodes.

10. The apparatus of claim 9 wherein said switching means comprises an electric switch carried by said housing that is in electrical communication with said electrical current source and said electrodes.

11. An apparatus for applying an electrical current to a tongue of a person for treating a substance addiction comprising:
   (a) a battery for providing a source of electrical current;
   (b) a housing having a compartment for receiving and retaining said battery therein;
   (c) a pair of spaced apart electrodes carried by the housing which are in electrical communication with said battery for delivering an electrical current to the tongue when both of said electrodes are in contact with the tongue, and wherein said housing, battery, and electrodes form an assembly that is grasped by hand during use; and
   (d) wherein said electrodes are constructed and arranged to contact the tip of the tongue to provide electrical current to the tongue for stimulating at least one hypoglossal nerve of the tongue.

12. The apparatus of claim 11 wherein said battery comprises a nine volt direct current battery.

13. The apparatus of claim 12 wherein said housing has an exterior surface with said electrodes being exposed through said exterior surface and further comprising the indicia "cocaine" carried by said exterior surface adjacent said electrodes.

14. The apparatus of claim 11 further comprising a circuit in electrical communication with said battery and said electrodes for (1) pulsing current applied to the tip of the tongue, or (2) oscillating current applied to the tip of the tongue for helping to treat cocaine addiction.

15. A method of treating a substance addiction of a person comprising:
   (a) providing an apparatus having a housing, an electrical current source in operable communication with the housing, and a pair of spaced apart electrodes carried by the housing;
   (b) applying the electrodes to the tongue of a person; and
   (c) applying an electrical current to the tongue.

16. The method of claim 15 comprising stimulating the tip of the tongue during application of current to treat an addiction to a substance that is one of the following: cocaine, food, cigarettes, chewing tobacco, nicotine, caffeine, marijuana, morphine, heroin, amphetamines, barbiturates, alcohol, and psychedelic drugs.

17. The method of claim 16 comprising the further steps of 1) constructing the housing to appear suggestive of the substance or nature of the addiction being treated and 2) the person viewing the housing before step (b).

18. The method of claim 17 comprising shaping the housing like a rock of cocaine.

19. The method of claim 17 comprising shaping the housing like a package of cigarettes.

20. The method of claim 17 comprising shaping the housing like a tin of chewing tobacco.

21. The method of claim 15 comprising holding the housing by hand during steps (b) and (c).

22. The method of claim 15 comprising during step (c) stimulating a hypoglossal nerve of the person by applying current to the tip of the tongue.

23. The method of claim 15 comprising during step (c) applying current to the tip of the tongue so as to stimulate a vagus nerve of the person to curb cravings for the substance of addiction.

24. The method of claim 15 comprising providing a housing with an exterior appearance suggestive of the substance of the addiction being treated and capable of being viewed by the person grasping the housing.

25. The method of claim 24 comprising repeating steps (b) and (c) upon the person experiencing a craving for the substance to which they are addicted.

26. A method of treating an addiction of a person comprising:
   (a) providing an electrical power source and at least two spaced apart electrodes in electrical communication with the electrical power source;
   (b) urging the electrodes into contact with the tongue of the person; and
   (c) administering an electrical stimulus to the tongue.

27. The method of claim 26 comprising during step (a) providing only two electrodes, and during step (b) urging the electrodes into contact with the tip of the tongue of the person.

28. The method of claim 27 comprising during step (c) administering direct current to the tongue.

29. The method of claim 27 comprising during step (c) administering alternating current to the tongue.

30. The method of claim 26 comprising during step (c) administering an electrical stimulus to the tip of the tongue.

31. The method of claim 26 comprising repeating steps (b) and (c) upon the person experiencing a craving for that to which they are addicted.

32. The method of claim 26 comprising providing a housing carrying the electrodes having an appearance suggestive of the addiction being treated and the step further comprising the person looking at the housing before contacting the electrodes to the tongue to associate the electrical stimulus with the addiction being treated.

33. An apparatus for applying a current to the mouth of a person to treat a substance addiction comprising:
   (a) a housing having an appearance suggestive of the substance being treated;
   (b) a source of electrical power;
   (c) a pair of spaced apart electrodes carried by the housing and which are electrically connected to said electrical source for delivering an electrical stimulus to the mouth when both of said electrodes are in contact with the mouth to treat the substance addiction.

34. The apparatus of claim 33 further comprising a label having an appearance suggestive of the addiction being treated wherein said label is carried by said housing.

35. The apparatus of claim 33 wherein 1) said electrical power source comprises a battery having a pair of output terminals, 2) said housing and electrodes are of unitary construction that is grasped by hand during use, and 3)

further comprising a compartment in said housing for receiving said battery and a pair of electrically conductive wires with i) one of said wires in electrical communication with one of said terminals of said battery and one of said electrodes and ii) the other of said wires in electrical communication with another of said terminals of said battery and the other of said electrodes.

36. The apparatus of claim 33 further comprising means for switching current flow to said electrodes.

37. An apparatus for applying an electrical stimulus to the tongue of a person comprising:
   (a) a housing having a compartment;
   (b) a battery received in said compartment and providing a source of electrical power;
   (c) a pair of electrodes spaced apart between one millimeter and two centimeters carried by said housing and which are electrically connected to said electrical power source for delivering an electrical stimulus to the tip of the tongue when both of said electrodes are in contact with the tip of the tongue; and
   (d) wherein said housing, battery and electrodes form a unitary assembly that is grasped by hand during use.

38. A method of delivering an electrical stimulus to treat a malady of a person comprising:
   (a) providing an electrical power source and at least two spaced apart electrodes in electrical communication with the electrical power source;
   (b) urging the electrodes into contact with the tongue of the person; and
   (c) administering an electrical stimulus to the tongue for treating an ulcer, gastritis, heartburn, excess stomach acid, stomach pain, or another stomach or gastric disorder.

39. The method of claim 38 comprising during step (c) administering the electrical stimulus to the tip of the tongue of the person.

40. A method of delivering an electrical stimulus to treat an eating disorder of a person comprising:
   (a) providing an electrical power source and at least two spaced apart electrodes receiving electrical power from the electrical power source;
   (b) urging the electrodes into contact with the tongue of the person; and
   (c) administering an electrical stimulus to the tongue.

41. The method of claim 40 comprising during step (c) administering the electrical stimulus to the tip of the tongue of the person.

42. A method of treating an addiction of a person comprising:
   (a) providing an apparatus having a housing, a pair of spaced apart electrodes carried by the housing, and a source of electricity electrically connected to the electrodes;
   (b) urging the pair of electrodes into contact with the tip of the tongue of the person; and
   (c) applying an electrical current to the tip of the tongue.

43. The method of claim 42 comprising repeating steps (b) and (c) upon the person experiencing a craving to smoke.

44. The method of claim 43 comprising providing a housing carrying the electrodes having an appearance suggestive of a tobacco product that is smoked and the step further comprising the person looking at the housing before contacting the electrodes to the tongue to associate the application of electrical current with tobacco.

45. The method of claim 42 comprising repeating steps (b) and (c) upon the person experiencing a craving for cocaine.

* * * * *